United States Patent [19]
Kotsugai

[11] Patent Number: 6,103,538
[45] Date of Patent: Aug. 15, 2000

[54] COLLOIDAL GOLD IMMUNOASSAY METHOD

[75] Inventor: Takeshi Kotsugai, Sawara, Japan

[73] Assignee: SS Pharmaceutical Co., Ltd., Tokyo, Japan

[21] Appl. No.: 08/973,747

[22] PCT Filed: May 29, 1996

[86] PCT No.: PCT/JP96/01446

§ 371 Date: Dec. 22, 1997

§ 102(e) Date: Dec. 22, 1997

[87] PCT Pub. No.: WO97/01099

PCT Pub. Date: Jan. 9, 1997

[30] Foreign Application Priority Data

Jun. 22, 1995 [JP] Japan ..................................... 7-177977

[51] Int. Cl.$^7$ .................................. G01N 33/533
[52] U.S. Cl. .......................... 436/536; 435/7.1; 435/7.92; 435/7.93; 435/7.94; 435/7.95; 435/962; 436/518; 436/523; 436/524; 436/526; 436/534; 436/537; 436/176; 436/826
[58] Field of Search ..................... 435/7.1, 7.92, 435/7.93, 7.94, 7.95, 962; 436/518, 523, 536, 524, 526, 534, 537, 176, 826

[56] References Cited

U.S. PATENT DOCUMENTS 5,108,933 4/1992 Liberti et al. .
5,225,326 7/1993 Bresser et al. .

*Primary Examiner*—Christopher L. Chin
*Assistant Examiner*—Bao-Thuy L. Nguyen
*Attorney, Agent, or Firm*—Oblon, Spivak, McClelland, Maier & Neustadt, P.C.

[57] ABSTRACT

Disclosed herein is a method for the detection of a target substance by a colloidal gold immunoassay, which comprises dissolving in an immunoreaction system a metal salt selected from the group consisting of sodium, potassium and lithium fluorides, sodium, potassium, lithium and magnesium iodides, sodium, potassium, lithium and magnesium bromides, lithium and magnesium chlorides, sodium, potassium, lithium and magnesium nitrates, sodium, potassium, lithium and magnesium sulfates, sodium, potassium, lithium and magnesium formates, sodium, potassium, lithium and magnesium acetates, and mixtures of at least two of these metal salts, whereby the metal salt is allowed to exist in a reaction mixture.

12 Claims, No Drawings

COLLOIDAL GOLD IMMUNOASSAY METHOD

This application is a 371 of PCT/JP96/01446 filed May 29, 1996.

TECHNICAL FIELD

This invention relates to an improvement in a colloidal gold immunoassay method for the determination of the presence or absence or the degree of presence of a target substance in a specimen, and especially to an improvement in a colloidal gold immunoassay method useful in the field of external diagnostics.

BACKGROUND ART

Detection of an antigen or an antibody by a colloidal gold immunoassay method is known for many years. The principle of this assay method is summarized as set out next. Namely, when a target substance is an antigen, for example, a colloidal gold which has been sensitized with an antibody capable of recognizing this antigen, that is, an antibody-sensitized colloidal gold is used in a reaction mixture containing, in general, the antigen and impurities and the like in an intimately mixed state, whereby the antibody-sensitized colloidal gold is specifically caused to bind to the antigen. A complex-containing reaction mixture, which contains a complex formed as a result of the reaction, is subjected to permeation like chromatographic development through a reaction mixture permeable material or to filtering permeation through a reaction mixture permeable material while making use of a diffusive infiltration phenomenon of the reaction mixture, so that the reaction mixture containing the complex, the antibody-sensitized colloidal gold, which has not reacted, and the impurities and the like are allowed to infiltratively move.

Further, by a capturing antibody which has been immobilized beforehand on the reaction mixture permeable material at a specific position on a moving path, binds specifically to the antigen and is different in antigen recognition site from the antibody-sensitized colloidal gold, the complex alone is captured at the specific position and the remaining matters are moved away along with the reaction mixture. By a color tone of the colloidal gold in the complex as appeared at the specific position, the antigen alone is distinguished or detected.

When the target is an antibody, on the other hand, a colloidal gold which has been sensitized with an antigen capable of recognizing the antibody (antigen-sensitized colloidal gold) is also reacted with the antibody by specific binding in a reaction mixture containing the antibody. Subsequently, the complex-containing reaction mixture which contains the resulting complex is caused to move through a reaction mixture permeable material by making use of a penetrative infiltration phenomenon as in the above-described detection. By either a capturing antibody or a capturing antigen which has been immobilized beforehand on the reaction mixture permeable material at a specific position and binds specifically to the antigen or antibody in the complex, only the complex out of the complex-containing reaction mixture is captured at the specific position. By a color tone of the colloidal gold in the complex as appeared at the specific position, the target antibody alone can be distinguished or detected.

In this colloidal gold immunoassay method, the specific binding is generally binding through an antigen-antibody reaction, and a usable colloidal gold is generally of the red type or the purple type.

The reaction mixture generally contains, as a medium, water which in turn contains biocomponents, buffer and the like. Water may be replaced in part by an inert water-soluble organic solvent such as dimethyl sulfoxide or dioxane with a view to assisting dissolution of the target substance in such a liquid-form medium, namely, liquid medium without interfering with the specific binding reaction. Further, an inert high-molecular substance may be added to protect the antibody or the like or to lower the dielectric constant of the reaction mixture containing the colloidal gold. Moreover, a surface active substance or the like can also be added for assisting the diffusive infiltration phenomenon of the reaction mixture.

As the reaction mixture permeable material, a sheet-like or laminate-like material equipped with permeability for the reaction mixture can be used. The target substance moves along with the reaction mixture by diffusive infiltration through interstices and pores in the material. This material is formed of at least one of sheets in the form of filter paper, cotton-like, sponge-like or porous films, and the like. The target substance is allowed to move generally in a coplanar direction in the case of a sheet-like material or in the direction of thickness in the case of a laminate-like material.

When the target substance in the colloidal gold immunoassay method is an antigen, it is general to use two types of antibodies for the antigen, to sensitize one of the antibodies, which is a monoclonal in general, with a colloidal gold into an antibody-sensitized colloidal gold, and to use the other antibody (either a monoclonal or a polyclonal), which is different in antigen recognition site from the antibody-sensitized colloidal gold, as a capturing antibody.

The colloidal gold immunoassay method will next be described in more detail on the basis of an example as applied for the detection of human chorionic gonadotropin (hCG) from human urine. For example, a piece of filter paper is used as a reaction mixture permeable material. A colloidal gold, which has been sensitized with an anti-hCG antibody (an anti-hCG monoclonal antibody labeled with colloidal gold particles), is held in a re-dissolvable (re-elutable) form near an end of the filter paper, whereas an anti-hCG polyclonal antibody or a monoclonal antibody different in antigen epitope from the above-described monoclonal antibody is immobilized as a capturing antibody in a form free from re-dissolution near an opposite end of the filter paper.

If needed for the confirmation of an end of development, a certain antibody for the above-described anti-hCG monoclonal antibody (for example, an anti-mouse IgG antibody if the monoclonal antibody is mouse IgG) is also immobilized at a position farther than a final end of the development as viewed in the direction of the development.

An assay is conducted by applying human urine, which contains the target substance, to the one end and then allowing the antigen and impurities to be developed along with the urine toward the opposite end by the diffusive infiltration phenomenon of the urine, which contains the antigen and the impurities and the like, in a similar manner as in paper chromatography.

By the development, the colloidal gold sensitized with the anti-hCG monoclonal antibody, said colloidal gold having been held near the one end, is first eluted into the urine. The colloidal gold and hCG, which is contained in the urine, forms an hCG-anti-hCG monoclonal antibody sensitized colloidal gold complex, which diffuses further toward the opposite end. This complex is captured by an antigen-antibody reaction with the immobilized capturing antibody, so that at the immobilized position of the capturing antibody, a color tone of the colloidal gold appears in an immobilized pattern (in the form of a spot, mark, letter or the like), thereby indicating the existence of hCG as the antigen in the urine.

On the other hand, the colloidal gold sensitized with the anti-hCG monoclonal antibody, which has been simply eluted in the urine and has not reacted with hCG, also diffuses along with the urine toward the opposite end. The unrealized conjugation is not ambushed behind antigen-antibody reaction with the capturing antibody and hence passes through the position of the capturing antibody. It is however captured by the anti-mouse IgG antibody immobilized near the final end, so that the color tone of the colloidal gold appears in an immobilized pattern (in the form of a spot, mark, letter or the like), thereby indicating that the development by the urine has been surely effected.

The colloidal gold immunoassay method is practiced under such a principle as described above and is used as a simple and easy assay method for substances in the body. This assay method however involves a problem in that the development of a color tone of a colloidal gold, said color tone being indicative of the results of a specific reaction for the detection of a target substance, is not always clear. There is hence a long standing desire for the development of a method which permits easy and clear recognition of a position colored with the colloidal gold without making darker a background color tone corresponding to a non-specific reaction.

DISCLOSURE OF THE INVENTION

With the foregoing circumstances in view, the present inventor has proceeded with various investigations in order to develop a method which assures clear appearance of a color tone of a colloidal gold. As a result, it has been found that an application of a simple measure, that is, mixing of an appropriate salt in a solution of a specimen or a solution for dissolving the specimen enables to make a color tone of a colloidal gold appear extremely vivid compared with the specimen solution or the specimen-dissolving solution without the salt, namely, an ordinary reaction mixture (a liquid medium for a specific binding reaction), leading to the completion of the present invention.

The present invention therefore provides a method for the detection of a target substance by a colloidal gold immunoassay, which comprises dissolving in an immunoreaction system a metal salt selected from the group consisting of sodium fluoride, potassium fluoride, lithium fluoride, sodium iodide, potassium iodide, lithium iodide, magnesium iodide, sodium bromide, potassium bromide, lithium bromide, magnesium bromide, lithium chloride, magnesium chloride, sodium nitrate, potassium nitrate, lithium nitrate, magnesium nitrate, sodium sulfate, potassium sulfate, lithium sulfate, magnesium sulfate, sodium formate, potassium formate, lithium formate, magnesium formate, sodium acetate, potassium acetate, lithium acetate and magnesium acetate and mixtures of at least two of these metal salts, whereby said metal salt is allowed to exist in a reaction mixture.

BEST MODES FOR CARRYING OUT THE INVENTION

The above-described metal salt in the present invention is a neutral salt of an alkali metal or alkaline earth metal. Other salts may also be present for buffering or as impurities or the like insofar as the object of the present invention can be achieved.

In the present invention, it is necessary to allow the above-described metal salt to exist in a reaction mixture in which an antigen-antibody reaction is induced in accordance with the colloidal gold immunoassay method, in other words, in a liquid-form medium, i.e., liquid medium containing a target substance. The metal salt may be added to a solution of a specimen or may be incorporated in a specimen-dissolving solution or a diluting solution.

No particular limitation is imposed on the concentration of the metal salt in the reaction mixture insofar as the development of a color tone of a colloidal gold becomes vivid. If the concentration is too low, the development of a color tone is not vivid, thereby failing to achieve the intended advantageous effect. If the concentration is too high, on the other hand, a non-specific reaction is promoted, leading to the development of problems in that the intended assay cannot be practiced and the immobilized antibody or the like is released. It is hence necessary to pay attention in this respect.

As the concentration in the reaction mixture at the time of an antigen-antibody reaction, the metal salt can generally be contained in the reaction mixture at a total concentration in a range of from 0.05 to 2 moles/liter, preferably from 0.05 to 1.5 moles/liter, more preferably from 0.1 to 1 mole/liter. If a salt having low solubility cannot by itself achieve a predetermined concentration, two or more salts can be used in combination.

Examples of the present invention will hereinafter be set out to describe the present invention more specifically. It should however be borne in mind that the present invention is not limited at all by these Examples.

EXAMPLE 1

Detection of Urine hCG (1) Kit:

A commercially-available pregnancy testing kit (Heart Sign hCG "New Type"; sold by SS Pharmaceutical Co., Ltd.), which detects urine hCG by a colloidal gold immunoassay method, was used.

This kit is composed of a reaction cassette, a dropping pipette and a urine sampling cup. The reaction cassette is internally provided with 16 mg of an anti-hCG mouse monoclonal antibody sensitized colloidal gold reagent in a sponge placed in a central hole and also with a judgment plate accommodated inside the reaction cassette at a location underneath the sponge in the central hole and carrying thereon 20 $\mu$g of an anti-hCG mouse antibody immobilized in the pattern of a heart. This kit is designed to allow successive passage of a urine specimen through the sponge and the judgment plate.

(2) Assay Principle and Detection Sensitivity:

The anti-hCG mouse monoclonal antibody sensitized colloidal gold binds via hCG to the anti-hCG mouse antibody immobilized on the judgment plate, so that the judgment plate is colored in a reddish purple to purple color. This coloration is observed with the naked eye to detect urine hCG. The detection sensitivity is 50 IU/liter.

(3) Test Specimen:

hCG (product of UCB-BioProducts) was added at a rate of 500 IU/liter to 250 ml of urine of a normal male subject.

(4) Addition of Salts:

The above specimen was poured in 5 ml-aliquots into 28 urine sampling cups, in which the following compounds were added and dissolved as metal salts, respectively, to give a concentration of 0.24 mole/liter-urine, whereby test specimens were prepared.

(Metal Salts)

Sodium fluoride, potassium fluoride, sodium iodide, potassium iodide, lithium iodide, magnesium iodide, sodium bromide, potassium bromide, lithium bromide, magnesium bromide, lithium chloride, magnesium chloride, sodium nitrate, potassium nitrate, lithium nitrate, magnesium nitrate, sodium sulfate, potassium sulfate, lithium sulfate, magnesium sulfate, sodium formate, potassium formate, lithium formate, magnesium formate, sodium acetate, potassium acetate, lithium acetate, and magnesium acetate.

The above specimen was poured in 5 ml-aliquots into 5 urine sampling cups. Without addition of any metal salt, one of the urine sampling cups was used as a control specimen (conventional method). As comparative specimens, sodium chloride, potassium chloride, ammonium chloride and ammonium acetate were added and dissolved at 0.24 mole/liter to the remaining urine sampling cups, respectively, in lieu of the above-described metal salts and the specimens so prepared were used (Comparative Examples 1–4).

(5) Assay:

Following instructions attached to the kit, urine is collected in a urine sampling cup, the urine is drawn up by suction to a graduation (mark) of a dropping pipette (0.5 ml ), and the urine inside the dropping pipette is then dropped in toto into the central hole of the reaction cassette. After waiting for about 1 minute, that is, after the urine has been entirely absorbed, a cover of the reaction cassette is opened and the judgment plate is taken out for judgment. The judgment is conducted based on the presence or absence of a heart mark rather than the density of a color tone. When a reddish purple heart mark is recognized centrally on a judgment surface subsequent to the completion of a reaction, a judgment of positivity shall be made. When no heart mark is recognized, a judgment of negativity shall be made.

In this Example, following the instructions, the respective specimens prepared in the procedure (4) were taken in 0.5 ml-aliquots and were then dropped into different reaction cassettes. Subsequent to absorption for 1 minutes, judgment plates were taken out, and heart-shaped, reddish purple spots appeared on central parts of respective judgment surfaces were judged and ranked with the naked eye in accordance with the following ranking system.

(Ranking System)

| [Score] | [Description] |
| --- | --- |
| +4 | Very strong color development is observed compared with the conventional method. |
| +3 | Strong color development is observed compared with the conventional method. |
| +2 | Slightly stronger color development is observed compared with the conventional method. |
| +1 | Color development of comparable strength with that of the conventional method is observed. |
| ± | Positivity cannot be judged due to poor color development. |

(6) Results:

The results will be presented next in Table 1. As is evident from the results, the addition of the metal salts in accordance with the present invention led to stronger and more vivid coloration compared with the conventional method, and hence to easier judgment.

TABLE 1

| Metal salt | Ranking |
| --- | --- |
| Sodium fluoride | +4 |
| Potassium fluoride | +4 |
| Sodium iodide | +2 |
| Potassium iodide | +3 |
| Lithium iodide | +3 |
| Magnesium iodide | +3 |
| Sodium bromide | +2 |
| Potassim bromide | +2 |
| Lithium bromide | +2 |
| Magnesium bromide | +2 |
| Lithium chloride | +3 |
| Magnesium chloride | +3 |
| Sodium nitrate | +2 |
| Potassim nitrate | +2 |
| Lithium nitrate | +2 |
| Magnesium nitrate | +3 |
| Sodium sulfate | +2 |
| Potassim sulfate | +3 |
| Lithium sulfate | +2 |
| Magnesium sulfate | +4 |
| Sodium formate | +3 |
| Potassim formate | +3 |
| Lithium formate | +3 |
| Magnesium formate | +3 |
| Sodium acetate | +3 |
| Potassim acetate | +3 |
| Lithium acetate | +3 |
| Magnesium acetate | +3 |
| Sodium chloride (Comp. Ex. 1) | +1 |
| Potassium chloride (Comp. Ex. 2) | +1 |
| Ammonium chloride (Comp. Ex. 3) | ± |
| Ammonium acetate (Comp. Ex. 4) | ± |
| None (Conventional method; control) | +1 |

EXAMPLE 2

Detection of Stool Human Hemoglobin (1) Kit:

A commercially-available test kit for hidden blood in stool [MEICHECK HEMOPLATE (GS); product of MEIJI SEIKA KAISHA, LTD.], which detects stool hemoglobin (hereinafter abbreviated as "Hb") by a colloidal gold immunoassay method, was used.

This kit is composed of a judgment plate, a colloidal gold reagent, a colloidal gold dissolving solution and a stool dissolving buffer and is provided with reaction containers, filters, a criterion photo, stool sampling containers and stool sampling sticks. Of these, the judgment plate contains 2.5 µg of an anti-Hb rabbit antibody. Further, the colloidal gold reagent contains an anti-Hb mouse monoclonal antibody labeled with the colloidal gold and is dissolved in the colloidal gold dissolving solution to furnish a reaction test solution. The stool dissolving buffer is contained in a 2 ml-aliquot in each stool sampling container.

(2) Assay Principle and Detection Sensitivity:

The anti-Hb mouse monoclonal antibody labeled with the colloidal gold binds via Hb to the anti-Hb rabbit antibody immobilized on a film of the judgment plate, so that the film is colored in a reddish-purple or purple color. This coloration is observed with the naked eye to detect stool Hb. The detection sensitivity is 40 µg/g-stool.

(3) Test Specimen:

Hb (product of Sigma Chemical Company) was added at a rate of 400 µg/g-stool to 1 g of stool of a normal human subject.

(4) Addition of Metal Salts:

The above specimen was collected in 10 mg-aliquots in 28 stool sampling containers which contained the stool dissolving buffer. To the containers, the following compounds were added and dissolved as metal salts, respectively, to give a concentration of 0.24 mole/liter-stool dissolving buffer, whereby test specimens were prepared.

(Metal Salts)

Sodium fluoride, potassium fluoride, sodium iodide, potassium iodide, lithium iodide, magnesium iodide, sodium bromide, potassium bromide, lithium bromide, magnesium bromide, lithium chloride, magnesium chloride, sodium nitrate, potassium nitrate, lithium nitrate, magnesium nitrate, sodium sulfate, potassium sulfate, lithium sulfate, magnesium sulfate, sodium formate, potassium formate, lithium formate, magnesium formate, sodium acetate, potassium acetate, lithium acetate, and magnesium acetate.

The above specimen was poured in 10 mg-aliquots into 5 stool sampling cups which contained the stool dissolving buffer. Without addition of any metal salt, one of the stool sampling containers was used as a control specimen solution (conventional method). As comparative specimen solutions, sodium chloride, potassium chloride, ammonium chloride and ammonium acetate were added and dissolved at 0.24 mole/liter to the remaining stool sampling containers, respectively, in lieu of the above-described metal salts (Comparative Examples 5–8).

(5) Assay:

Following instructions, 50 µl-aliquots of the respective specimen solutions prepared in the procedure (4) are taken and then dropped into different reaction containers. To the respective reaction containers, 40 µl-aliquots of the reaction test solution are added dropwise, and the reaction containers are shaken several times to mix the respective specimen solutions with the reaction test solution. The judgment plates are placed over the respective reaction containers, and with the judgment plates held gently, the reaction containers were left over at room temperature for 3 minutes. The reaction containers are turned upside down, and through the transparent reaction containers, judgment surfaces are observed with the naked eye.

A judgment is made on the basis of a degree of coloration of a judgment mark (star shape) appeared on each judgment surface by comparing the coloration with the positivity limit of the criterion photo. When distinct coloration (reddish-purple or purple) is observed on the judgment surface, stool Hb is judged to be positive. When no coloration or only slight coloration is observed on the judgment surface compared with the positive limit of the criterion photo, stool Hb is judged to be negative. Through a comparison with the control specimen solution, effects of the addition of the metal salts were judged and ranked in accordance with the following ranking system.

(Ranking System)

| [Score] | [Description] |
| --- | --- |
| +4 | Very strong color development is observed compared with the conventional method. |
| +3 | Strong color development is observed compared with the conventional method. |
| +2 | Slightly stronger color development is observed compared with the conventional method. |
| +1 | Color development of comparable strength with that of the conventional method is observed. |
| ± | Positivity cannot be judged due to poor color development. |

(6) Results:

The results will be presented next in Table 2. As is evident from the results, the addition of the metal salts in accordance with the prevent invention led to stronger and more vivid coloration compared with the conventional method, and hence to easier judgment.

TABLE 2

| Metal salt | Ranking |
| --- | --- |
| Sodium fluoride | +3 |
| Potassium fluoride | +3 |
| Sodium iodide | +2 |
| Potassium iodide | +2 |
| Lithium iodide | +3 |
| Magnesium iodide | +3 |
| Sodium bromide | +3 |
| Potassim bromide | +3 |
| Lithium bromide | +3 |
| Magnesium bromide | +3 |
| Lithium chloride | +3 |
| Magnesium chloride | +3 |
| Sodium nitrate | +2 |
| Potassim nitrate | +2 |
| Lithium nitrate | +2 |
| Magnesium nitrate | +3 |
| Sodium sulfate | +2 |
| Potassim sulfate | +2 |
| Lithium sulfate | +2 |
| Magnesium sulfate | +2 |
| Sodium formate | +3 |
| Potassim formate | +3 |
| Lithium formate | +3 |
| Magnesium formate | +3 |
| Sodium acetate | +3 |
| Potassim acetate | +3 |
| Lithium acetate | +3 |
| Magnesium acetate | +3 |
| Sodium chloride (Comp. Ex. 5) | +1 |
| Potassium chloride (Comp. Ex. 6) | +1 |
| Ammonium chloride (Comp. Ex. 7) | ± |
| Ammonium acetate (Comp. Ex. 8) | ± |
| None (Conventional method; control) | +1 |

EXAMPLE 3

Detection of Urine hCG at Various Metal Salt Concentrations (1) Kit:

As in Example 1, the commercially-available pregnancy testing kit (Heart Sign HCG "New Type"), which detects urine hCG by the colloidal gold immunoassay method, was used.

(2) Test Specimen:

The test specimen prepared in the procedure (3) of Example 1 was used.

(3) Addition of Metal Salts:

The above specimen was poured in 5 ml-aliquots into 13 urine sampling cups, to which as salts, sodium fluoride was added to give concentrations of 0.06, 0.12, 0.48 and 0.96 mole/liter-urine, potassium fluoride was added to give concentrations of 0.06, 0.12, 0.48 and 0.96 mole/liter-urine, and lithium fluoride was added to give a concentration of 0.06 mole/liter and further, sodium fluoride and potassium fluoride were added at an equimolar ratio to give total concentrations of 0.12, 0.24, 0.96 and 1.92 moles/liter-urine, respectively. As a control, a 5 ml-aliquot of the above specimen was poured into a urine sampling cup and was used without addition of any metal salt (conventional method).

(4) Assay and Judgment:

Similarly to Example 1, each assay was conducted following the instructions attached to the kit, and ranking was performed in a similar manner as in Example 1.

(5) Results:

The results will be presented next in Table 3. As is evident from the results, the addition of the metal salts in accordance with the present invention led to stronger and more vivid coloration compared with the conventional method, and hence to easier judgment.

TABLE 3

| Metal salt | Conc. | Ranking |
| --- | --- | --- |
| Sodium fluoride | 0.06 | +2 |
| ditto | 0.12 | +3 |
| ditto | 0.48 | +3 |
| ditto | 0.96 | +2 |
| Potassium fluoride | 0.06 | +2 |
| ditto | 0.12 | +3 |
| ditto | 0.48 | +3 |
| ditto | 0.96 | +2 |
| Sodium fluoride + pottasium fluoride | 0.12 | +3 |
| ditto | 0.24 | +4 |
| ditto | 0.96 | +2 |
| ditto | 1.92 | +2 |
| Lithium fluoride | 0.06 | +2 |
| None (Conventional method; control) | | +1 |

CAPABILITY OF EXPLOITATION IN INDUSTRY

In the detection of an antigen or antibody by a colloidal gold immunoassay method, the addition of a metal salt to a reaction mixture in accordance with the method of the present invention enhances coloration by colloidal gold compared with the conventional method, in which such a salt is not added, and the examples, in which other salts were added, as demonstrated above by way of example. Specifically, the color development of the colloidal gold becomes very vivid owing to the function of the metal salt and, especially when a specimen of a concentration around a detection limit is observed with the naked eye, a difference between negativity and positivity becomes clearer. Accordingly, the present invention exhibits marked advantageous effects in that a judgment can be made with ease.

I claim:

1. A method of detecting a substance by immunoassay, comprising:

adding to a specimen a metal salt selected from the group consisting of sodium fluoride, potassium fluoride, lithium fluoride, sodium iodide, potassium iodide, lithium iodide, magnesium iodide, sodium bromide, potassium bromide, lithium bromide, magnesium bromide, lithium chloride, magnesium chloride, sodium nitrate, potassium nitrate, lithium nitrate, magnesium nitrate, sodium sulfate, potassium sulfate, lithium sulfate, magnesium sulfate, sodium formate, potassium formate, lithium formate, magnesium formate, sodium acetate, potassium acetate, lithium acetate and magnesium acetate, and mixtures thereof;

contacting the specimen containing the metal salt with a colloidal gold having an antigen or an antibody immobilized thereon, wherein the antigen or an antibody forms a complex with the substance, when the substance is present in the sample;

isolating the complex, when formed; and assaying the amount of isolated complex and correlating the amount of isolated complex with the presence or absence of the substance in the specimen.

2. The method of claim 1, wherein the metal salt is selected from the group consisting of sodium fluoride, potassium fluoride, lithium iodide, magnesium iodide, lithium chloride, magnesium chloride, magnesium nitrate, magnesium sulfate, sodium formate, potassium formate, lithium formate, magnesium formate, sodium acetate, potassium acetate, lithium acetate and magnesium acetate or a mixture of at least two of these metal salts.

3. The method of claim 1, wherein the metal salt is selected from the group consisting of sodium fluoride, potassium fluoride or a mixture thereof.

4. The method of claim 1, wherein the metal salt is sodium fluoride.

5. The method of claim 1, wherein the concentration of the metal salt in the specimen is 0.05 to 2 moles per liter.

6. The method of claim 1, wherein the concentration of the metal salt in the specimen is 0.1 to 1 moles per liter.

7. The method of claim 1, wherein the colloidal gold is sensitized with an antigen.

8. The method of claim 7, wherein substance is an antibody which binds to the antigen.

9. The method of claim 1, wherein the colloidal gold is sensitized with an antibody.

10. The method of claim 9, wherein substance is an antigen which binds to the antibody.

11. The method of claim 1, wherein the specimen contains a detectable amount of the substance.

12. The method of claim 1, wherein the absence of a detectable quantity of the complex correlates with the absence of the substance in the specimen.

* * * * *